United States Patent
Ooga et al.

(10) Patent No.: US 10,335,612 B2
(45) Date of Patent: Jul. 2, 2019

(54) PARTICLE BEAM TREATMENT SYSTEM, PARTICLE BEAM TREATMENT METHOD, AND COMPUTER PROGRAM PRODUCT

(71) Applicant: Kabushiki Kaisha Toshiba, Minato-ku (JP)

(72) Inventors: Junichiro Ooga, Kawasaki (JP); Hideki Ito, Kawasaki (JP); Nobukatsu Sugiyama, Kawasaki (JP); Atsuro Oonishi, Yokohama (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 728 days.

(21) Appl. No.: 14/846,160

(22) Filed: Sep. 4, 2015

(65) Prior Publication Data

US 2016/0082284 A1 Mar. 24, 2016

(30) Foreign Application Priority Data

Sep. 19, 2014 (JP) ................................ 2014-191837

(51) Int. Cl.
*A61N 5/10* (2006.01)
(52) U.S. Cl.
CPC ........... *A61N 5/107* (2013.01); *A61N 5/1049* (2013.01); *A61N 5/1037* (2013.01); *A61N 5/1078* (2013.01); *A61N 2005/1087* (2013.01)
(58) Field of Classification Search
CPC .. A61N 5/1049; A61N 5/1064; A61N 5/1069; A61N 5/107; A61N 5/1078
See application file for complete search history.

(56) References Cited

U.S. PATENT DOCUMENTS

| 6,937,696 B1 * | 8/2005 | Mostafavi ............ A61B 5/113 378/65 |
| 8,457,379 B2 | 6/2013 | Tashiro et al. |
| 2007/0201613 A1 | 8/2007 | Lu et al. |

(Continued)

FOREIGN PATENT DOCUMENTS

| JP | 07-246245 | 9/1995 |
| JP | H07-303710 | 11/1995 |

(Continued)

*Primary Examiner* — Carrie R Dorna
(74) *Attorney, Agent, or Firm* — Oblon, McClelland, Maier & Neustadt, L.L.P.

(57) ABSTRACT

According to an embodiment, a particle beam treatment system includes a storage, an estimator, a target value generator, and a particle beam treatment device. The storage stores therein a respiratory movement model obtained by synchronizing amount of displacement of an affected area of a subject with a signal related to respiration of the subject and performing modeling. The estimator estimates, based on the measured signal related to respiration and the respiratory movement model, amount of displacement of the affected area corresponding to the measured signal. The target value generator generates a target value, which is used for performing movement control on a platform on which the subject is lying down, corresponding to the estimated amount of displacement of the affected area. The particle beam treatment device irradiates, with particle beams, the affected area of the subject on the platform subjected to movement control according to the target value.

5 Claims, 7 Drawing Sheets

(56) References Cited

U.S. PATENT DOCUMENTS

| | | |
|---|---|---|
| 2008/0212737 A1 | 9/2008 | D'Souza et al. |
| 2009/0110238 A1 | 4/2009 | Li et al. |
| 2009/0252291 A1* | 10/2009 | Lu .................... A61N 5/1049 378/65 |
| 2011/0266464 A1 | 11/2011 | Takai et al. |
| 2012/0181428 A1 | 7/2012 | Bert et al. |
| 2013/0211482 A1 | 8/2013 | Piipponen |
| 2014/0031602 A1 | 1/2014 | Fujimoto et al. |

FOREIGN PATENT DOCUMENTS

| | | |
|---|---|---|
| JP | 2005-074156 A | 3/2005 |
| JP | 2006-51199 A | 2/2006 |
| JP | 2006-314643 | 11/2006 |
| JP | 2008-104790 | 5/2008 |
| JP | 2009-502245 A | 1/2009 |
| JP | 2011-500263 A | 1/2011 |
| JP | 2011-130859 | 7/2011 |
| JP | 2012-196326 | 10/2012 |
| JP | 2012-532711 | 12/2012 |
| JP | 2013-540554 | 11/2013 |
| JP | 2014-042815 | 3/2014 |
| JP | 2014-054302 | 3/2014 |
| JP | 2015-142671 A | 8/2015 |
| WO | WO 2010/058863 A1 | 5/2010 |

\* cited by examiner

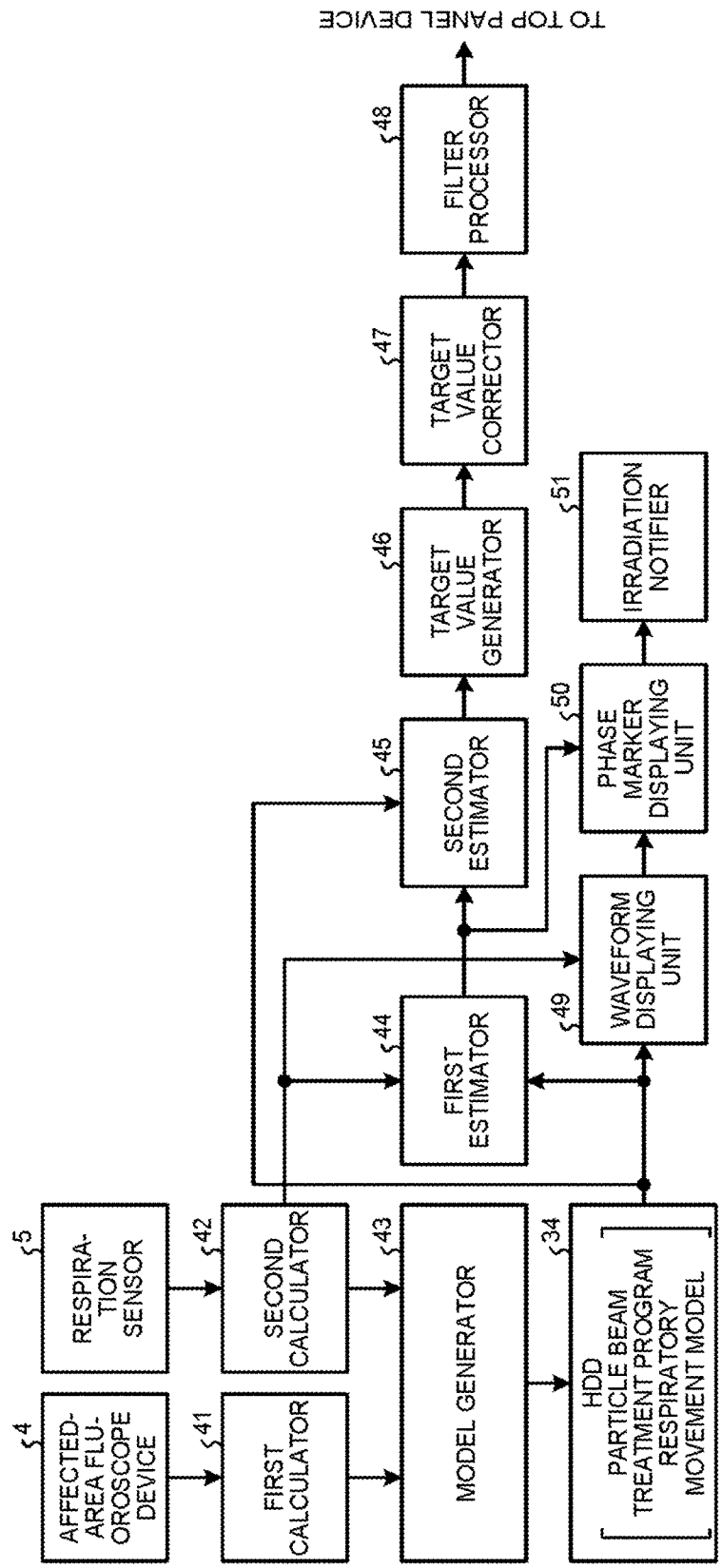

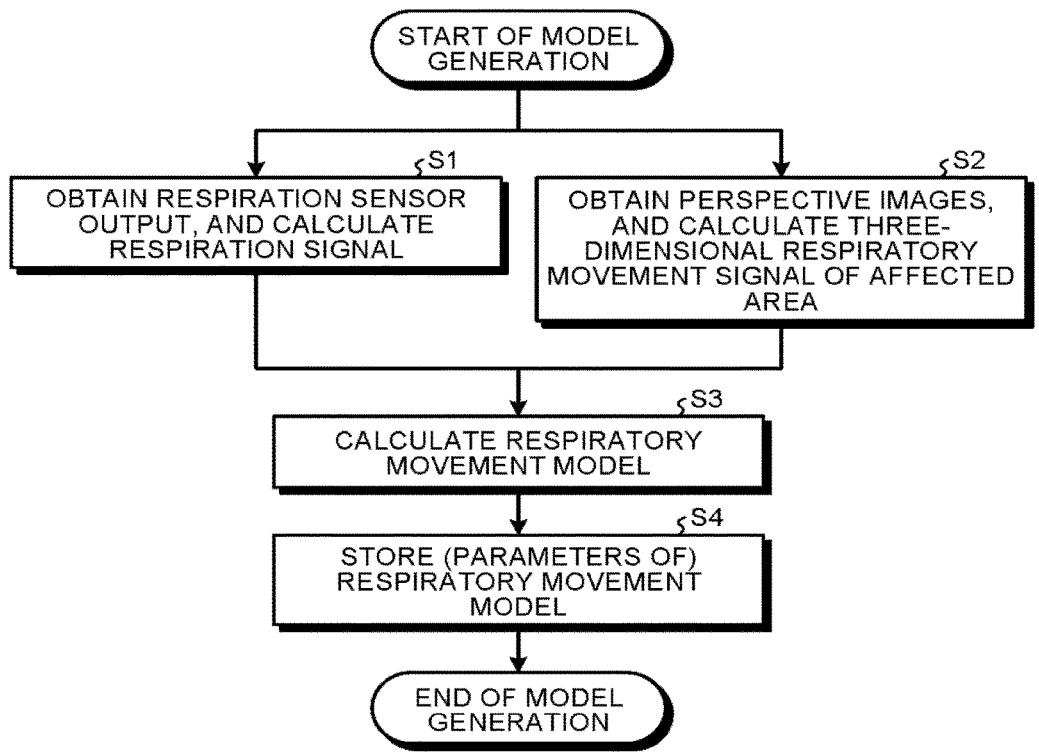
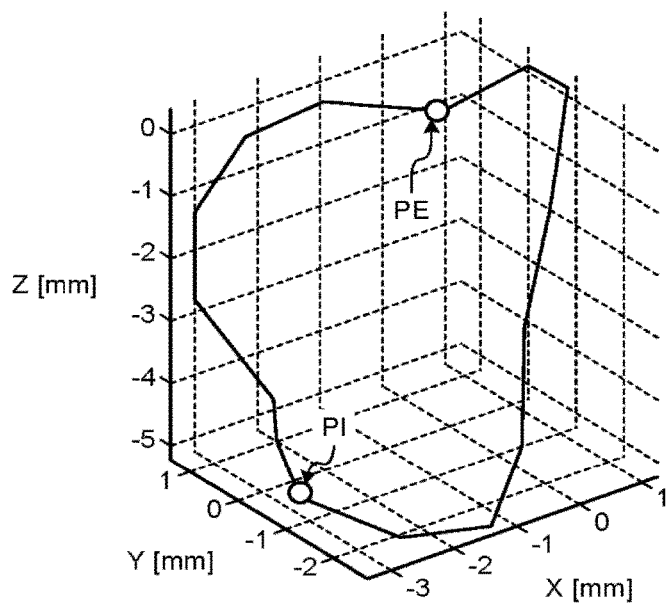

PARTICLE BEAM TREATMENT SYSTEM, PARTICLE BEAM TREATMENT METHOD, AND COMPUTER PROGRAM PRODUCT

CROSS-REFERENCE TO RELATED APPLICATIONS

This application is based upon and claims the benefit of priority from Japanese Patent Application No. 2014-191837, filed on Sep. 19, 2014; the entire contents of which are incorporated herein by reference.

FIELD

An embodiment described herein relates generally to a particle beam treatment system, a particle beam treatment method, and a computer program product.

BACKGROUND

These days, cancer treatment using particle beams is known in which protons or heavy ions such as carbon ions are accelerated to about 70% of the velocity of light and are delivered with surgical precision onto the focus of a refractory cancer. While performing cancer treatment using particle beams, based on the treatment program implemented prior to the treatment, the positioning of the treatment table on which the patient is made to lie down is determined in such a way that the affected area is present at the irradiation position of the particle beams. As compared to the X rays used in radiation therapy, the dose of particle beams becomes higher in the deeper portion of the body (particle beams have the Bragg peak). Hence, as compared to the radiation therapy, the cancer treatment using particle beams can be performed with a smaller number of times of irradiation. Moreover, near the surface of the body, the dose of particle beams having the Bragg peak is smaller. Hence, in the cancer treatment using particle beams, the irradiation with particle beams can be done for a plurality of number of times while avoiding skin burn.

The tissues in the body, such as lungs or liver, perform cyclic movement attributed to the effect of respiration and cardiac motion. Such movement of the body tissues differs from person to person. Not only that, in the same person too, the movement of the body tissues changes every day, every week, or every year.

For that reason, in the conventional cancer treatment using particle beams, irradiation with the particle beams is done at the timing of switching between expiration and inhalation, which is the timing at which the movement and the shape of the affected area undergoes only a small change in synchronization with the respiration cycle (gating irradiation method). That is, in the gating irradiation method, the affected area is irradiated with particle beams at the timings in between expiration and inhalation.

However, in the gating irradiation method, since the irradiation with the particle beams are done only at the timings in between expiration and inhalation, the irradiation with the particle beam becomes intermittent in nature. For that reason, in the gating irradiation method, the treatment time becomes longer.

BRIEF DESCRIPTION OF THE DRAWINGS

FIG. 2 is a functional block diagram of the functions implemented when a CPU performs operations according to a particle beam treatment program in the dynamic tracking therapy system according to the embodiment;

FIG. 3 is a flowchart for explaining a flow of operations performed while generating a respiratory movement model in the dynamic tracking therapy system according to the embodiment;

FIG. 4 is a diagram illustrating the three-dimensional movement zone and the amount of movement of the affected area corresponding to the states of respiration of a test subject;

DETAILED DESCRIPTION

According to an embodiment, a particle beam treatment system includes a storage, an estimator, a target value generator, and a particle beam treatment device. The storage stores therein a respiratory movement model, which is obtained by synchronizing amount of displacement of an affected area of a test subject with a signal related to respiration of the test subject and performing modeling. The estimator estimates, based on the signal related to respiration that is measured and the respiratory movement model, amount of displacement of the affected area corresponding to the signal related to respiration that is measured. The target value generator generates a target value, which is used for performing movement control on a platform on which the test subject is lying down, corresponding to the estimated amount of displacement of the affected area. The particle beam treatment device irradiates, with particle beams, the affected area of the test subject who is lying down on the platform which is subjected to movement control according to the target value.

Explained below as an example is a dynamic tracking therapy system according to an embodiment in which a particle beam treatment system, a particle beam treatment method, and a computer program product are implemented.

Figure 1:
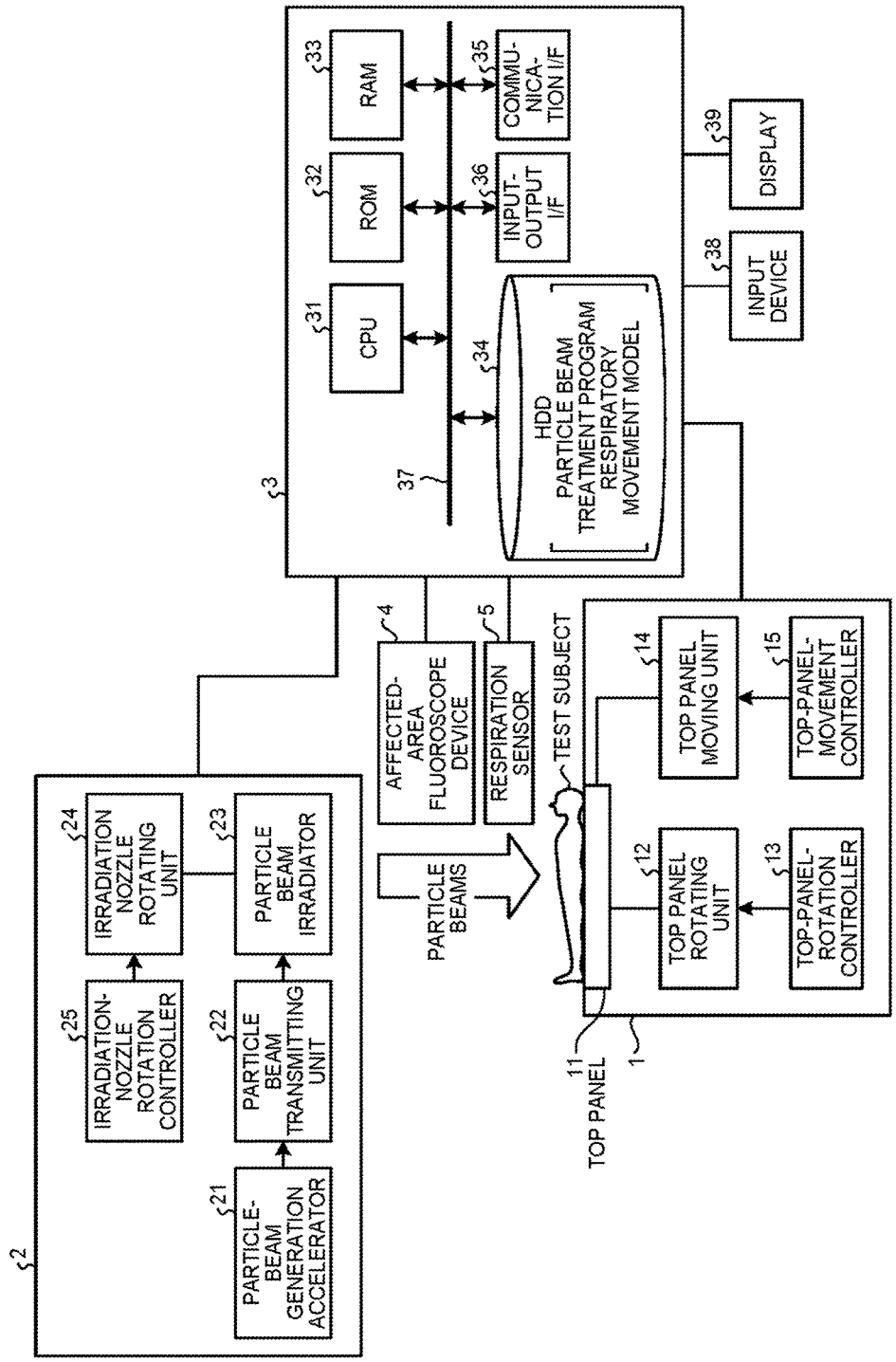
FIG. 1 is a system configuration diagram of a dynamic tracking therapy system according to an embodiment.

FIG. 1 is a system configuration diagram of the dynamic tracking therapy system according to the embodiment. As illustrated in FIG. 1, the dynamic tracking therapy system includes a top panel device 1, a particle beam treatment device 2, an information processing device 3, an affected-area fluoroscope device 4, and a respiration sensor 5.

The top panel device 1 includes a top panel 11, a top panel rotating unit 12, a top-panel-rotation controller 13, a top panel moving unit 14, and a top-panel-movement controller 15. The top panel 11 is an example of a platform. The top panel 11 is plate-like in shape and has a size sufficient to make a test subject lie down parallel to the floor. Thus, on the top panel 11, the test subject for particle beam treatment is made to lie down. The plane on which the test subject is made to lie is herein referred to as a "mounting plane". The top panel 11 is translated by the top panel moving unit 14 either in the body axis direction of the test subject who is lying down or in the orthogonal direction to the body axis direction. Moreover, the top panel 11 is subjected to rotational transfer in the mounting plane by the top panel rotating unit 12. Meanwhile, herein, the orthogonal direction to the body axis direction is simply referred to as "orthogonal direction".

The top panel moving unit 14 is connected to the top-panel-movement controller 15. The top panel moving unit 14 includes a translation mechanism for translating the top panel 11 either in the body axis direction of the test subject or in the orthogonal direction; and includes a motor that drives the translation mechanism. More particularly, the top-panel-movement controller 15 performs drive control with respect to the motor of the top panel moving unit 14. Consequently, the top panel 11 moves either in the body axis direction of the test subject or in the orthogonal direction. For example, the motor of the top panel moving unit 14 rotates a rotating member such as a gear. That leads to the movement of a horizontal-movement member engaged with the gear moves, thereby leading to the translation of the top panel 11.

The top panel rotating unit 12 includes a disk for rotating the top panel moving unit 14 and the top panel 11 in a plane parallel to the top panel 11, and includes a motor that drives the disk. The top-panel-rotation controller 13 drives the motor of the top panel rotating unit 12, and rotates the top panel 11 and the top panel moving unit 14 around the irradiation center in a plane parallel to the top panel 11.

Herein, as a method of irradiating the affected area of the test subject with particle beams, a "scanning method" is known in which, a scanning electromagnet is used and position control of narrow beams (pencil beams) of particle beams is performed in the horizontal direction and the vertical direction with respect to slice surfaces of the affected area; and the particle beams are emitted in such a way that the affected area is filled by the beam spots of the pencil beams. Moreover, in the scanning method, the movement of the beam spots among the slice surfaces (movement in the depth direction) is achieved using a range shifter. Alternatively, in the scanning method, the movement of the beam spot among the slice surfaces (movement in the depth direction) is achieved by controlling the energy of the pencil beams in a stepwise manner and moving what is called the Bragg peak of the particle beams in the depth direction.

However, in a sense, the scanning method represents an irradiation method for controlling the particle beams. Hence, the energy efficiency undergoes a decline. Particularly, in the case of irradiating slice surfaces in the back with the particle beams, it becomes necessary to drastically increase the energy of the pencil beams, thereby making the issue of a decline in the energy efficiency more prominent.

In that regard, in the dynamic tracking therapy system according to the embodiment, the irradiation position and the irradiation energy of the pencil beams of particle beams are kept fixed. Then, in the dynamic tracking therapy system according to the embodiment, the top panel 11 is subjected to movement control as described later, and the irradiation position of particle beams is controlled with respect to the slice surfaces of the affected area and the depth direction. More particularly, in the dynamic tracking therapy system according to the embodiment, when the test subject is irradiated with particle beams from above, the top panel 11 on which the test subject is lying down is moved from side to side, and the irradiation position of the pencil beams is controlled within the slice surfaces. Moreover, in the dynamic tracking therapy system according to the embodiment, when the test subject is irradiated with particle beams from above, the top panel 11 on which the test subject is lying down is moved in the direction parallel to the travelling direction (the irradiation direction) of the particle beams. With that, the irradiation position of the pencil beams among the slice surfaces (in the depth direction) is controlled.

The particle beam treatment device 2, which is an example of a particle beam treatment unit, includes a particle-beam generation accelerating unit 21, a particle beam transmitting unit 22, a particle beam irradiator (an irradiation nozzle) 23, an irradiation nozzle rotating unit (a rotating gantry) 24, and an irradiation-nozzle rotation controller 25.

The particle-beam generation accelerating unit 21 is connected to the particle beam transmitting unit 22, and includes an ion source and accelerators such as a linear accelerator, a cyclotron, and a synchrotron. The particle-beam generation accelerating unit 21 generates positive ions such as hydrogen ions, helium ions, carbon ions or neon ions using the ion source. Moreover, the particle-beam generation accelerating unit 21 accelerates the positive ions up to a predetermined energy using the accelerators. That is, in the particle-beam generation accelerating unit 21, the positive ions are accelerated using a linear accelerator and then the positive ions coming out from the linear accelerator are further accelerated using a synchrotron. With that the positive ions get accelerated up to a predetermined energy. Then, the particle-beam generation accelerating unit 21 shoots out the positive ions, which have been accelerated up to a predetermined energy, to the particle beam transmitting unit 22.

The particle beam transmitting unit 22 is connected to the particle-beam generation accelerating unit 21 and the particle beam irradiator 23, and includes a beam path that is continuous from the particle-beam generation accelerating unit 21 to the particle beam irradiator 23. More particularly, the particle beam transmitting unit 22 transmits the positive ions, which come out from the particle-beam generation accelerating unit 21, to the particle beam irradiator 23 through the beam path.

The particle beam irradiator 23 emits the positive ions, which are transmitted from the particle beam transmitting unit 22, toward the test subject. At that time, the particle beam irradiator 23 emits the particle beams toward the irradiation center (isocenter).

Then, the information processing device 3 performs a reconfiguration operation for reconfiguring perspective images (described later) and performs a calculation operation for calculating the target position of the top panel 11. As the information processing device 3, it is possible to use a general-purpose computer device. The information processing device 3 includes a CPU 31, a ROM 32, a RAM 33, and a hard disk drive (HDD) 34. Herein, the HDD 34 is an example of a storage. In addition, the information processing device 3 includes a communication interface (communication I/F) 35 and an input-output interface (input-output I/F) 36. Moreover, the CPU 31 to the input-output I/F 36 are interconnected via a bus line 37. Meanwhile, CPU stands for "Central Processing Unit"; ROM stands for "Read Only Memory"; and RAM stands for "Random Access Memory".

Meanwhile, to the information processing device 3 are connected an input device 38, such as a keyboard and a mouse, and a display 39, such as a liquid crystal monitor device. Moreover, to the information processing device 3 are connected the affected-area fluoroscope device 4, which sees through the affected area of the test subject, and the respiration sensor 5, which detects respiration of the test subject and outputs a respiration signal. Herein, the respiration signal is an example of a signal related to respiration. Moreover, a respiration phase represents the division on the time axis of a period from expiration to inhalation of respiration that occurs in a cyclic manner. Although described later, on the display 39, a graph of respiration signals is displayed that indicates the states of respiration of the test subject, and a respiratory movement model is displayed that indicates the respiration-based movement zone of the affected area. Moreover, a phase marker is displayed that indicates the movement zone of the affected area corresponding to the state of respiration of the test subject.

The affected-area fluoroscope device 4 performs continuous imaging of the affected area from a plurality of directions in order to detect in time series the three-dimensional movements of the affected area. More particularly, the affected-area fluoroscope device 4 can be configured using, for example, a plurality of X-ray tubes and X-ray detectors. Alternatively, as the affected-area fluoroscope device 4, it is possible to use an X-ray computed tomogram (CT) imaging device or a magnetic resonance imaging (MRI) device. That is, as long as continuous imaging of the affected area from a plurality of directions is possible, any device can be used as the affected-area fluoroscope device 4.

In the information processing device 3, a particle beam treatment program is stored in the HDD 34. The CPU 31 performs operations according to the particle beam treatment program, and carries out particle beam treatment while moving the top panel 11 according to the state of respiration of the test subject and the respiration-based movement zone of the affected area.

FIG. 2 is a functional block diagram of the functions implemented when the CPU 31 performs operations according to the particle beam treatment program. As illustrated in FIG. 2, the CPU 31 includes a first calculator 41, a second calculator 42, a model generator 43, a first estimator 44, a second estimator 45, a target value generator 46, a target value corrector 47, and a filter processor 48. Moreover, the CPU 31 includes a waveform displaying unit 49, a phase marker displaying unit 50, and an irradiation notifier 51.

The first calculator 41 calculates a respiratory movement signal that indicates the amount of movement of the affected area attributed to respiration. The second calculator 42 calculates a respiration signal that indicates the state of respiration of the test subject. The model generator 43 generates a respiratory movement model in which the respiratory signals are associated with the respiratory movement signals, which indicate the amount of movement of the affected area attributed to respiration. The first estimator 44 estimates the current respiration phase from the respiratory movement model. The second estimator 45 estimates, from the respiratory movement model, the amount of displacement of the affected area corresponding to the state of respiration. The target value generator 46 generates a target value for the purpose of moving the top panel 11 in the direction of movement and by a distance equivalent to the amount of movement corresponding to the estimated amount of displacement of the affected area corresponding to the state of respiration. The target value corrector 47 corrects the target value to a value in which the control delay is taken into account. The filter processor 48 holds down the target value to a value within an appropriate range.

Meanwhile, in this example, the explanation is given under the assumption that the CPU 31 executes the particle beam treatment program and implements the first calculator 41 to the irradiation notifier 51 in the form of software. However, alternatively, some or all of the constituent elements from the first calculator 41 to the irradiation notifier 51 can be implemented using hardware.

The particle beam treatment program can be recorded as an installable or executable file in a computer-readable recording medium such as a CD-ROM or a flexible disk (FD). Alternatively, the particle beam treatment program can be recorded in a computer-readable recording medium such as a CD-R, a DVD, a Blu-ray disc (registered trademark), or a semiconductor memory. Herein, DVD stands for "Digital Versatile Disk". Still alternatively, the particle beam treatment program can be provided in the form of a downloadable file from a network such as the Internet. Still alternatively, the particle beam treatment program can be stored in advance in a ROM of a device.

The first calculator 41 calculates, from the captured images of the affected area that are obtained by the affected-area fluoroscope device 4 by performing continuous imaging of the affected area from a plurality of directions, the three-dimensional movements of the affected area in time series. The second calculator 42 calculates a respiration signal from the detection output of the respiration of the test subject as detected by the respiration sensor 5. Moreover, the second calculator 42 may also performing filter processing for the purpose of noise removal.

The model generator 43 generates in advance, for example, before the start of particle beam treatment, a respiratory movement model that indicates the movement zones of the affected area corresponding to the states of respiration; and stores the respiratory movement model in the HDD 34. More particularly, the model generator 43 associates the respiration signals, which are calculated by the second calculator 42 and which indicate the states of respiration, with the respiratory movement signals, which are calculated by the first calculator 41 and which indicate the movement zones of the affected area. Then, the model generator 43 stores, in the HDD 34, the parameters of the respiration signal and the parameters of the respiratory movement signal as a respiratory movement model. Meanwhile, since the movement of the affected area changes according to the "day" or the "time slot", it is desirable that the respiratory movement model is generated immediately before the start of particle beam treatment. However, alternatively, the respiratory movement model can be generated a few days before or a few hours before.

During the particle beam treatment, the first estimator 44 compares the current respiration signal with the respiratory movement model stored in the HDD 34, and estimates the respiration phase of the current respiration signal. The second estimator 45 estimates the amount of movement (the amount of displacement) of the affected area corresponding to the estimated respiration phase. The target value generator 46 generates a target value of the direction of movement and the amount of movement of the top panel 11 corresponding to the estimated amount of movement of the affected area. The target value corrector 47 corrects the target value to a value in which the control response delay time is taken into account. The filter processor 48 performs filter processing with respect to the target value if it becomes too prominent due to noise; corrects the target value to a value within a normal range; and sends the corrected value to the top panel device 1.

The waveform displaying unit 49 displays the current respiration signal waveform of the test subject as detected by the respiration sensor 5 as well as displays the respiratory movement model stored in the HDD 34 on the display 39.

The phase marker displaying unit 50 displays a phase marker, which indicates the current phase, on the respiration signal waveform and the respiratory movement model that are displayed on the display 39. The irradiation notifier 51 notifies the surrounding users about the irradiation with particle beams while the particle beams are being emitted (i.e., while the treatment is underway using particle beams). As an example, while the particle beams are being emitted, the irradiation notifier 51 displays a text "under irradiation" or a corresponding icon on the display 39. Alternatively, while the particle beams are being emitted, the irradiation notifier 51 outputs a sound indicating the irradiation with particle beams or performs drive-control with respect to a vibrator. Herein, it is possible to perform either one or many of displaying a text, outputting a sound, and driving a vibrator.

In such a dynamic tracking therapy system, in the case of performing particle beam treatment by tracking the movement of the affected area that moves under the effect of the movements attributed to respiration; firstly, a respiratory movement model is generated before starting the particle beam treatment and is stored in the HDD 34. The respiratory movement model represents the parameters indicating the movement zones of the affected area corresponding to the states of respiration. Herein, it is desirable that the respiratory movement model is generated immediately before the start of particle beam treatment. However, alternatively, the respiratory movement model can be generated in advance such as a few hours before, a few days before, or a few weeks before.

FIG. 3 is a flowchart for explaining a flow of operations performed while generating a respiratory movement model. Upon receiving an instruction via the input device 38 to generate a respiratory movement model, the CPU 31 of the information processing device 3 follows the particle beam treatment program stored in the HDD 34; functions as the first calculator 41 to the model generator 43 illustrated in FIG. 2; and generates (identifies) a respiratory movement model.

The explanation is given step by step. At Step S1, the second calculator 42 illustrated in FIG. 2 obtains the respiration sensor output indicating the state of respiration of the test subject as detected by the respiration sensor 5, and calculates a respiration signal indicating the state of respiration.

At Step S2, the first calculator 41 calculates the movement zone and the amount of movement of the affected area that moves due to respiration. More particularly, the affected-area fluoroscope device 4 is configured using a plurality of X-ray tubes and X-ray detectors as described above. Alternatively, the affected-area fluoroscope device 4 is configured using an X-ray computed tomogram (CT) imaging device. The affected-area fluoroscope device 4 performs continuous imaging of the affected area. With that, the three-dimensional movements of the affected area can be detected in time series. Moreover, the first calculator 41 calculates, from a plurality of captured images (perspective images) of the affected area that are obtained by the affected-area fluoroscope device 4 by performing continuous imaging, a respiratory movement signal indicating the three-dimensional movement zone and the amount of movement of the affected area.

Figure 5:
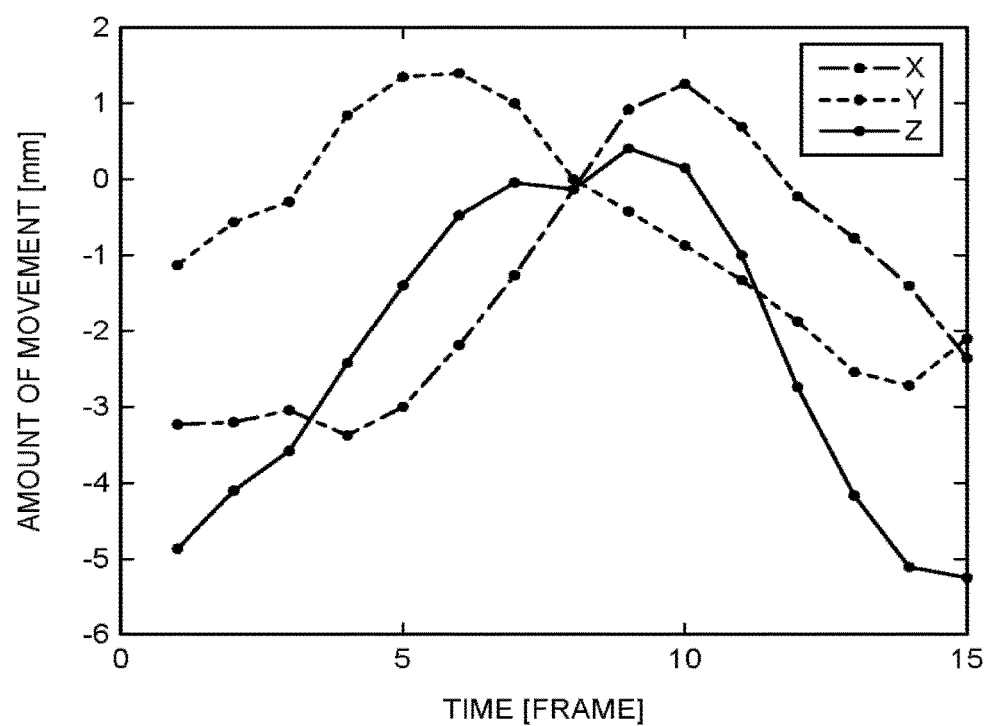
FIG. 5 is a diagram illustrating graphs representing the amount of movement of the affected area in time series in the XYZ directions.

Then, at Step S3, the model generator 43 generates a respiratory movement model using the fact that the respiration signals calculated by the second calculator 42 and the respiratory movement signals calculated by the first calculator 41 are obtained in synchronization. Meanwhile, the movement of the affected area as represented by the respiratory movement model is cyclic in nature. In FIG. 4 is illustrated the three-dimensional movement zone and the amount of movement of the affected area corresponding to the states of respiration. In the graph illustrated in FIG. 4, "PE" represents the peak of expiration and "PI" represents the peak of inhalation. In FIG. 5 are illustrated graphs representing the amount of movement of the affected area in time series in the XYZ directions. In FIG. 5, the graph illustrated with a dashed-dotted line represents the amount of movement of the affected area in time series in the X-axis direction. Moreover, in FIG. 5, the graph illustrated with a chained line represents the amount of movement of the affected area in time series in the Y-axis direction. Furthermore, in FIG. 5, the graph illustrated with a solid line represents the amount of movement of the affected area in time series in the Z-axis direction.

As an example, the model generator 43 makes use of the cyclic nature of the movement of the affected area and calculates the respiratory movement model using an autoregressive model (AR model). In the AR model, from a finite number of sets of past time-series data, the current estimated value can be calculated using the same finite number of parameters. That is, if p number of parameters $a_1, \ldots, a_p$ are used with respect to p number of sets of part time-series data $y(t-1), \ldots, y(t-p)$; then a current estimated value y_hat(t) can be calculated using Equation (1) given below.

$$y\_hat(t) = -a_1 y(t-1) - a_2 y(t-2) \ldots -a_p y(t-p) + e(t) \quad (1)$$

Figure 6:
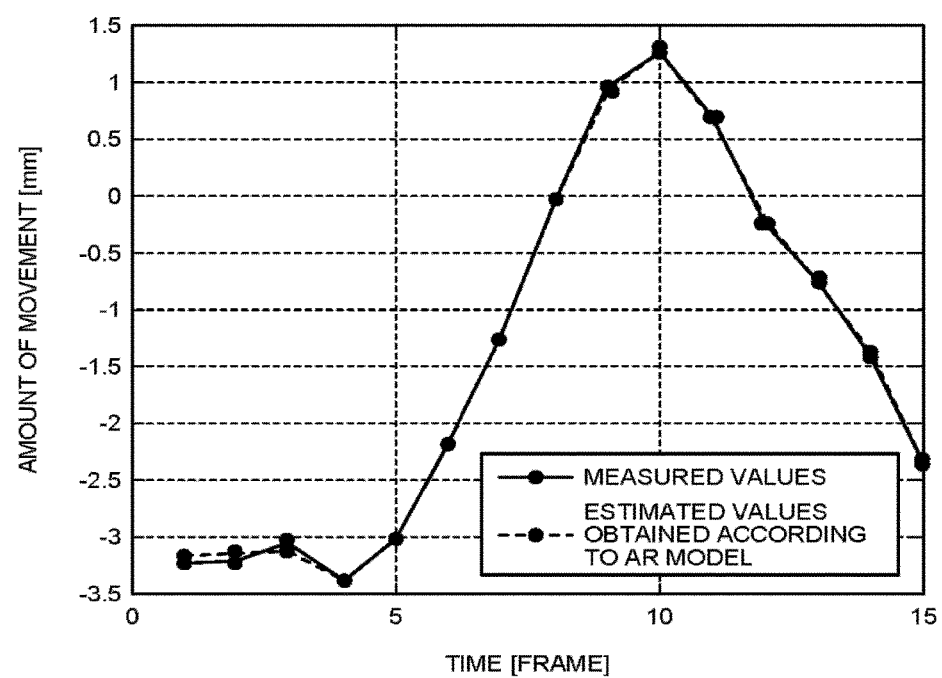
FIG. 6 is a diagram illustrating measured values of the amount of movement of the affected part and illustrating estimated values of the amount of movement of the affected part as obtained according to an AR model.

In Equation (1), "e(t)" represents an estimation error. Moreover, in Equation (1), "t" implies that the data is sampled in a discrete manner. In the AR model, the method of least squares is implemented to determine a finite number parameters in such a way that the estimation error is the smallest. A graph illustrated with a solid line in FIG. 6 represents the graph of measured values of actual measurement of the amount of movement of the affected area. On the other hand, a graph illustrated with a dotted line in FIG. 6 represents the graph of measured values of the amount of movement of the affected area as obtained according to the AR model. By comparing the solid-line graph and the dotted-line graph, it can be seen that the AR model used in estimating the amount of movement of the affected area is almost unchanged from the graph of actual measured values.

At Step S4, the model generator 43 performs control to store the parameters of the respiratory movement model in the HDD 34. That marks the end of the operations performed while generating a respiratory movement model as illustrated in the flowchart in FIG. 3.

Figure 7:
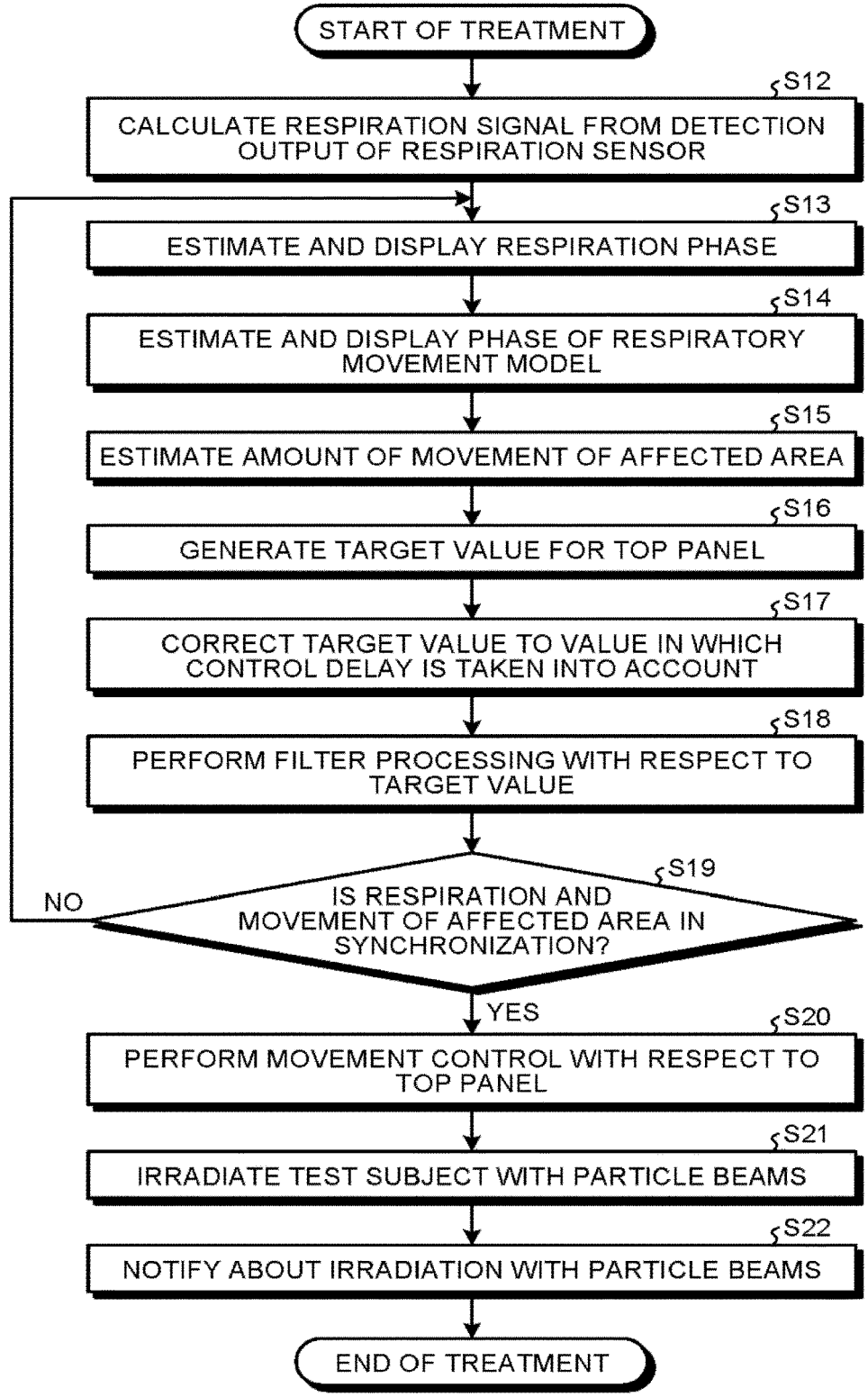
FIG. 7 is a flowchart for explaining a flow of operations performed during the particle beam treatment in which the respiratory movement model is used.

FIG. 7 is a flowchart for explaining a flow of operations performed during the particle beam treatment in which the respiratory movement model is used. Firstly, at Step S12, the second calculator 42 illustrated in FIG. 2 calculates the current respiration signal of the test subject from the detection output regarding the respiration of the test subject as detected by the respiration sensor 5.

Then, at Step S13, the first estimator 44 refers to the respiration signal calculated by the second calculator 42 and refers to the parameters constituting the respiratory movement model stored in the HDD 34, and estimates the respiration phase of the current respiration signal. More particularly, the first estimator 44 creates an AR model in which the sequence of parameters of the respiratory movement model is shifted one by one. Then, as the AR model in which the should-be-estimated respiration phase is expressed (i.e., as the respiratory movement model), the first estimator 44 estimates the AR model at the time when the difference between the estimated value and the current value after the input of a respiration signal is the smallest. In other words, the first estimator 44 performs evaluation about which estimated value of the AR model (the respiratory movement model) has the current value of the respiration signal closest thereto, and accordingly estimates the respiration phase. That is, since the respiratory movement model is generated by synchronizing the movement of the affected area with the respiration signals, the first estimator 44 compares the estimated value of each item in the AR model (the respiratory movement model) with the current value of the respiration signal, and estimates the estimated value closest to the current value of the respiration signal as the respiration phase. The waveform displaying unit 49 displays the respiration signal of the estimated respiration phase in a manner described later.

Then, at Step S14, the second estimator 45 takes into account the estimated respiration phase and creates an AR model by shifting the parameters constituting the respiratory movement model; and estimates the respiratory movement signal of the affected area. Herein, the estimation can also be done using the respiratory movement signals of the past. The waveform displaying unit 49 displays the estimated respiratory movement signal in a manner described later.

Figure 8:
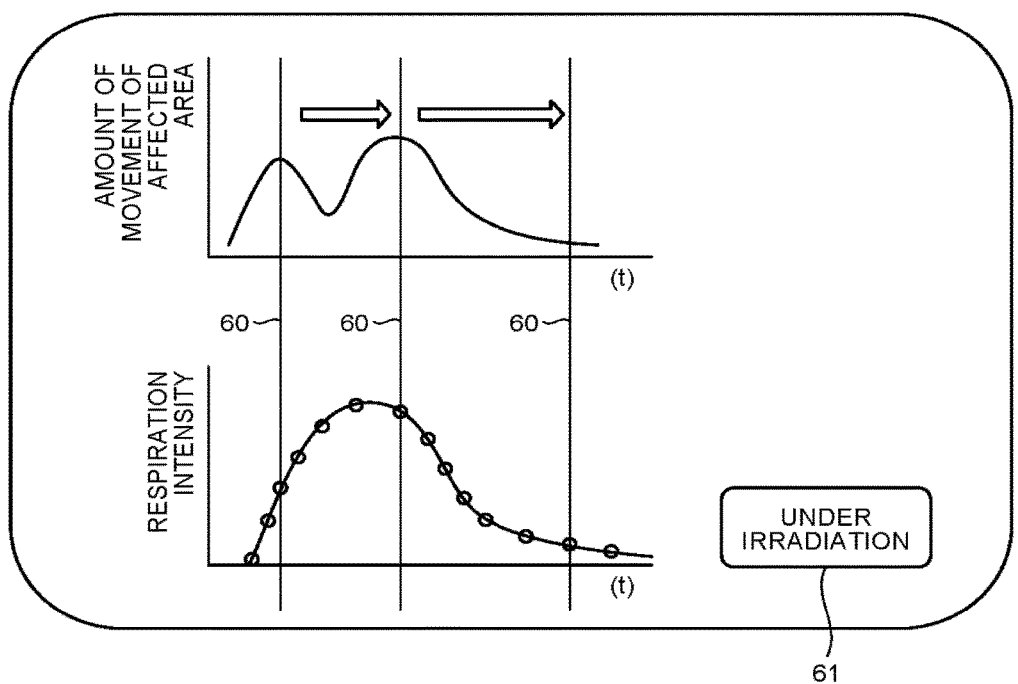
FIG. 8 is a diagram illustrating display examples of a signal waveform of the respiration signals and a waveform of the respiratory movement model that are displayed by a waveform displaying unit.

In FIG. 8 are illustrated display examples of a signal waveform of the respiration signals and a waveform of the respiratory movement model that are displayed by the waveform displaying unit 49. In the example illustrated in FIG. 8, the waveform illustrated in the upper part represents the waveform of the respiratory movement model (the waveform of the amount of movement of the affected area in time series). Moreover, in the example illustrated in FIG. 8, the waveform illustrated in the lower part represents the waveform of the respiration signals (the waveform of the respiration intensity in time series). The phase marker displaying unit 50 performs movement display control with respect to a phase marker 60 illustrated in FIG. 8 between the signal waveform of the respiration signals and the waveform of the respiratory movement model in synchronization with the current value of the respiration signal calculated by the second calculator 42. That is, every time the current value of the respiration signal is calculated by the second calculator 42, the phase marker displaying unit 50 moves the phase marker 60 to such a position on the waveform of the respiration signals which corresponds to the calculated current value of the respiration signal.

The signal waveform of the respiration signals as displayed by the waveform displaying unit 49 and the waveform of the respiratory movement model are waveforms having synchronized phases. Hence, when the phase marker 60 is moved to such a position on the waveform of the respiration signals which corresponds to the calculated current value of the respiration signal, the phase marker 60 not only indicates the calculated current value of the respiration signal but also indicates the current amount of movement of the affected area.

As a therapy device having such a display format implemented therein, it is possible to have a therapy device performing treatment using something other than particle beams. That is, a therapy device having such a display format implemented therein includes a treatment unit for treating the affected area by irradiating it with radiation or particle beams, and includes a respiration waveform displaying unit that displays a respiration signal waveform. Moreover, the therapy device includes a respiratory-movement-model displaying unit that displays the waveform of a respiratory movement model indicating the amount of movement of the affected area. Furthermore, the therapy device includes a marker displaying unit that displays a marker indicating the current respiration phase and the current amount of movement of the affected area. Moreover, the therapy device includes a notifier that notifies about the irradiation of radiation or particle beams while the radiation or the particle beams are being emitted on the test subject.

Subsequently, at Step S15, from the estimated respiratory movement signal of the affected area, the second estimator 45 estimates the amount of displacement. At Step S16, using the estimated amount of displacement of the affected area, the target value generator 46 calculates a control target value for the top panel 11. Herein, while performing position control with respect to the top panel 11, there occurs a control delay between the target value and the current value. When a control delay occurs, at the time when the top panel 11 reaches the target value, the position of the affected area moves to a different position from the anticipated position thereby leading to the possibility of an error in the irradiation position of particle beams. For that reason, at Step S17, the target value corrector 47 corrects the control target value of the top panel 11 to a value in which the control delay is taken into account. As a result, the control delay can be absorbed and the particle beams can be emitted while the affected area is present at the anticipated position. That enables prevention of an adverse situation in which an error occurs in the irradiation position of the particle beams.

Meanwhile, if the target value indicating the movement zone of the top panel 11 changes by a large margin as compared to the previous target value, then the top panel 11 is likely to vibrate. Hence, at Step S18, the filter processor 48 performs filter processing so that the corrected target value is equal to or smaller than a predetermined value. As a result, it becomes possible to avoid an adverse situation in which the target value indicating the movement zone of the top panel 11 changes by a large margin as compared to the previous target value thereby leading to vibration of the top panel 11.

Then, at Step S19, the CPU 31 refers to the current respiration signal calculated by the second calculator 42, the estimated value of the respiration phase as estimated by the first estimator 44, and the estimated amount of movement of the affected area as estimated by the second estimator 45; and determines whether or not the respiration is in synchronization with the movement of the affected area. If the CPU 31 determines that the respiration is not in synchronization with the movement of the affected area (No at Step S19), then the system control returns to Step S13, and estimation of the phase of the respiration signal and estimation of the phase of the respiratory movement model is performed in a repeated manner until the respiration falls in synchronization with the movement of the affected area.

On the other hand, if the CPU 31 determines that the respiration is in synchronization with the movement of the affected area (Yes at Step S19), then the system control proceeds to Step S20 and the target value of the top panel 11 that has been subjected to filter processing by the filter processor 48 is sent to the top panel device 1. Then, in the top panel device 1, the top-panel-movement controller 15 and the top-panel-rotation controller 13 perform movement control with respect to the top panel 11 according to the target value via the top panel rotating unit 12 and the top panel moving unit 14, respectively.

Subsequently, at Step S21, the CPU 31 performs irradiation control of particle beams with respect to the test subject, who is lying down on the top panel 11 that has been subjected to movement control according to the target value, via the particle beam treatment device 2. In the dynamic tracking therapy system according to the embodiment, the irradiation position and the irradiation energy of the pencil beams of the particle beams are kept fixed. Moreover, by performing movement control with respect to the top panel 11 according to the target value, the treatment is carried out while controlling the irradiation position of the particle beams with respect to the slice surfaces and the depth direction of the affected area.

More particularly, in the dynamic tracking therapy system according to the embodiment, when the particle beams are irradiated from above the test subject, the top panel 11 on which the test subject is lying down is moved from side to side. As a result, the treatment is carried out while controlling the irradiation position of the pencil beams within the slice surfaces. Moreover, in the dynamic tracking therapy system according to the embodiment, when the particle beams are irradiated from above the test subject, the top panel 11 on which the test subject is lying down is moved up and down parallel to the travelling direction (the irradiation direction) of the particle beams. As a result, the treatment is carried out while controlling the irradiation position of the pencil beams among the slice surfaces (in the depth direction).

In the dynamic tracking therapy system according to the embodiment, the test subject lying down on the top panel 11 is moved by tracking the movement of the affected area that moves due to respiration. Hence, particle beam treatment can be carried out by moving the irradiation position of particle beams within the slice surfaces and the among the slice surfaces (in the depth direction). Hence, the affected area can be continuously irradiated with particle beams for treatment purposes, thereby enabling achieving shortening of the treatment time.

Once the affected area is irradiated with the particle beams, the irradiating notifier 51 illustrated in FIG. 2 notifies about the irradiation with particle beams at Step S22. That marks the end of the operations illustrated in the flowchart in FIG. 7. In FIG. 8 is illustrated an example of a particle-beam irradiation notification operation. In the example illustrated in FIG. 8, the irradiation notifier 51 displays an icon having a text "under irradiation" on the display 39. As a result, the operator can be notified about the fact that particle beams are being emitted. Herein, the text "under irradiation" can be displayed in a blinking or illuminated manner on the display 39. Alternatively, a sound notifying the irradiation can be output. Still alternatively, a vibrator can be driven. Still alternatively, some or all of the abovementioned options can be used in combination in the notification operation.

As can be understood from the explanation given above, in the dynamic tracking therapy system according to the embodiment, the movement of the affected area is synchronized with the respiration signals and modeling is performed (a respiratory movement model is identified). Moreover, during the irradiation with particle beams, the respiration phase is estimated from the calculated respiration signal, and the amount of displacement of the affected area is estimated from the respiratory movement model (i.e., respiratory movement amount estimation is performed). Furthermore, from the estimation of the movement of the affected area, the target value for moving the top panel 11 is generated. Then, upon keeping the irradiation position and the irradiation energy of the particle beams fixed, the movement control with respect to the top panel 11 is performed according to the generated target value, and the affected area of the test subject is irradiated with the particle beams.

As a result, it becomes possible to perform tracking irradiation in which the movement of the affected area is captured in a continuous manner, thereby enabling achieving shortening of the treatment time.

While a certain embodiment has been described, the embodiment has been presented by way of example only, and is not intended to limit the scope of the inventions. Indeed, the novel embodiment described herein may be embodied in a variety of other forms; furthermore, various omissions, substitutions and changes in the form of the embodiment described herein may be made without departing from the spirit of the inventions. The accompanying claims and their equivalents are intended to cover such forms or modifications as would fall within the scope and spirit of the inventions.

What is claimed is:

1. A particle beam treatment system comprising:
one or more hardware processors configured to function as:
a first calculator configured to calculate a respiratory movement signal indicative of an amount of displacement of an affected area attributed to respiration of a test subject, from a plurality of captured images in which a movement of the affected area is captured;
a second calculator configured to calculate a signal related to respiration of the test subject from a respiration detection output of a respiration sensor;
a model generator configured to generate a respiratory movement model obtained by synchronizing the respiratory movement signal with the signal related to respiration of the test subject and performing modeling;
an estimator configured to compare a measured signal related to respiration with the respiratory movement model, estimate a respiration phase of the measured signal related to respiration, and estimate the amount of displacement of the affected area corresponding to the estimated respiration phase;
a target value generator configured to generate a target value, which is used for performing movement control on a platform on which the test subject is lying down, on the basis of the estimated amount of displacement of the affected area;
a target value corrector configured to correct the target value in such a way that a control delay with respect to a position of the platform is absorbed;
an irradiation controller configured to control a particle beam treatment device to irradiate, with particle beams, the affected area of the test subject who is lying down on the platform which is subjected to movement control according to the target value that is corrected; and
a phase marker displaying unit configured to display, on a display, a phase marker indicative of a position of the affected area in accordance with the respiratory movement model and a signal waveform of the measured signal related to respiration.

2. The system according to claim 1, wherein, in the particle beam treatment device, irradiation position and irradiation energy of pencil beams of particle beams are kept fixed.

3. The system according to claim 1, wherein an autoregressive model is used as the respiratory movement model.

4. A particle beam treatment method comprising:
calculating a respiratory movement signal indicative of an amount of displacement of an affected area attributed to respiration of a test subject, from a plurality of captured images in which a movement of the affected area is captured;

calculating a signal related to respiration of the test subject from a respiration detection output of a respiration sensor;

generating a respiratory movement model obtained by synchronizing the respiratory movement signal with the signal related to respiration of the test subject and performing modeling;

comparing a measured signal related to respiration with the respiratory movement model;

estimating a respiration phase of the measured signal related to respiration;

estimating the amount of displacement of the affected area corresponding to the estimated respiration phase;

generating a target value, which is used for performing movement control on a platform on which the test subject is lying down, on the basis of the estimated amount of displacement of the affected area;

correcting the target value in such a way that a control delay with respect to a position of the platform is absorbed;

controlling a particle beam treatment device to irradiate, with particle beams, the affected area of the test subject who is lying down on the platform which is subjected to movement control according to the target value that is corrected; and displaying, on a display, a phase marker indicative of a position of the affected area in accordance with the respiratory movement model and a signal waveform of the measured signal related to respiration.

5. A computer program product comprising a non-transitory computer-readable medium including a particle beam treatment program, wherein the particle beam treatment program, when executed by a computer, causes the computer to function as:

a first calculator configured to calculate a respiratory movement signal indicative of an amount of displacement of an affected area attributed to respiration of a test subject, from a plurality of captured images in which a movement of the affected area is captured;

a second calculator configured to calculate a signal related to respiration of the test subject from a respiration detection output of a respiration sensor;

a model generator configured to generate a respiratory movement model obtained by synchronizing the respiratory movement signal with the signal related to respiration of the test subject and performing modeling;

an estimator to compare a measured signal related to respiration with the respiratory movement model, estimate a respiration phase of the measured signal related to respiration, and estimate the amount of displacement of the affected area corresponding to the estimated respiration phase;

a target value generator to generate a target value, which is used for performing movement control on a platform on which the test subject is lying down, on the basis of the estimated amount of displacement of the affected area;

a target value corrector configured to correct the target value in such a way that a control delay with respect to a position of the platform is absorbed;

an irradiation controller configured to control a particle beam treatment device to irradiate, with particle beams, the affected area of the test subject who is lying down on the platform which is subjected to movement control according to the target value that is corrected; and a phase marker displaying unit to display, on a display, a phase marker indicative of a position of the affected area in accordance with the respiratory movement model and a signal waveform of the measured signal related to respiration.

* * * * *